(12) United States Patent
Ishikura

(10) Patent No.: US 7,695,139 B2
(45) Date of Patent: Apr. 13, 2010

(54) ALIGNMENT METHOD FOR OPHTHALMIC MEASUREMENT APPARATUS AND ALIGNMENT DEVICE OF THE SAME

(75) Inventor: Yasuhisa Ishikura, Itabashi-ku (JP)

(73) Assignee: Kabushiki Kaisha TOPCON, Itabashi-ku, Tokyo (JP)

( * ) Notice: Subject to any disclaimer, the term of this patent is extended or adjusted under 35 U.S.C. 154(b) by 606 days.

(21) Appl. No.: 11/645,746

(22) Filed: Dec. 27, 2006

(65) Prior Publication Data
US 2007/0146636 A1 Jun. 28, 2007

(30) Foreign Application Priority Data
Dec. 28, 2005 (JP) ............... 2005-378585

(51) Int. Cl.
*A61B 3/14* (2006.01)
(52) U.S. Cl. ............ 351/208; 351/206; 351/210; 351/221
(58) Field of Classification Search ................. 351/208
See application file for complete search history.

(56) References Cited

U.S. PATENT DOCUMENTS

| | | | |
|---|---|---|---|
| 5,382,988 A | 1/1995 | Nanjo | |
| 5,502,521 A * | 3/1996 | Katou | 351/221 |
| 5,889,576 A | 3/1999 | Fujieda | |
| 5,975,698 A * | 11/1999 | Iijima | 351/208 |
| 6,494,577 B2 * | 12/2002 | Iwanaga | 351/208 |
| 2003/0151720 A1 | 8/2003 | Chernyak et al. | |
| 2004/0169818 A1 * | 9/2004 | Hoshino | 351/205 |
| 2004/0184000 A1 * | 9/2004 | Hayashi | 351/222 |
| 2004/0189936 A1 * | 9/2004 | Mimura et al. | 351/205 |

FOREIGN PATENT DOCUMENTS

| | | |
|---|---|---|
| EP | 0 931 504 A1 | 7/1999 |
| EP | 1 452 128 A1 | 9/2004 |
| JP | 04-297226 A | 10/1992 |
| JP | 06-007292 A | 1/1994 |
| JP | P3606706 B2 | 10/2004 |

OTHER PUBLICATIONS

Extended European Search Report, European Application No. 06026866.1-1265, dated Apr. 3, 2008.

* cited by examiner

*Primary Examiner*—Jessica T Stultz
(74) *Attorney, Agent, or Firm*—Buchanan Ingersoll & Rooney PC

(57) ABSTRACT

An alignment device for an ophthalmic measurement apparatus including an index projection optical system that forms a plurality of indices on a cornea of an eye to be examined by projecting a plurality of index lights onto the cornea; an imaging optical system that forms the images of the plurality of indices on an imaging device as index images; a three-dimensional driving device for driving the imaging optical system in a three-dimensional direction; and a controlling device for controlling to drive the three-dimensional driving device.

17 Claims, 6 Drawing Sheets

ALIGNMENT METHOD FOR OPHTHALMIC MEASUREMENT APPARATUS AND ALIGNMENT DEVICE OF THE SAME

This application is based on and claims priority from Japanese Patent Application No. 2005-378585, filed on Dec. 28, 2005, the disclosure of which is incorporated herein by reference in its entirety.

BACKGROUND OF THE INVENTION

1. Field of the Invention

The present invention relates to an alignment method for an ophthalmic measurement apparatus in which alignment of a measuring optical system is required for an eye to be examined of a patient, and an alignment device thereof.

2. Description of the Related Art

As an alignment method for an ophthalmic measurement apparatus equipped with an automatic alignment function, several alignment methods have been conventionally known.

There is known an apparatus in which alignment is manually performed that a front eye portion of an eye to be examined is image-captured by an imaging device of an imaging optical system, the front eye portion of the eye to be examined is displayed on a display device such as a monitor television or the like by the image signal from the imaging device, the imaging optical system is moved horizontally and vertically by operating an operation lever such as a joy stick or the like to manually move the center of a pupil of the eye to be examined toward the center of the imaging device being the center of the display device, and then, the imaging optical system is operated to move back and forth by the operation lever, and a working distance between the eye to be examined and the imaging optical system is adjusted so as to make the front eye portion of the eye to be examined sharp.

In this manual alignment, since the work of matching the optical axis of the imaging optical system with the cornea vertex (visual axis) of the eye to be examined is performed based on examiner's intuition, an alignment work is not easy. As a device for solving the problem, there is known an automatic refractometer, a tonometer or the like, where index light is projected onto the cornea of the eye to be examined so as to form a bright spot image (index image) at the half position of a radius of curvature of the cornea, the bright spot image is formed on a two-dimensional light-receiving device such that this bright spot image becomes the cornea vertex of the eye to be examined, a photographing optical system is driven horizontally and vertically by three-dimensional driving device to allow the bright spot image to move toward the center of the imaging device, and automatic alignment is performed.

However, in this automatic alignment constitution, a region where a light-receiving device can detect the bright spot image formed by reflected light from the cornea is narrow, there is a room for improvement.

Specifically, when the bright spot image comes off from a detection region where automatic alignment can be performed and reflected light cannot be detected in the initial state, it is necessary that an examiner manually operate to move the imaging optical system via the operation lever (joy stick) horizontally and vertically to perform rough alignment in a direction where the bright spot image matches the approximately central portion of the light-receiving device until the measuring optical system (ophthalmic unit) comes in a detection region with respect to the eye.

This causes a load to the examiner operating the system and could prevent quick measurement. As one solution to this problem, a method of expanding a detection region of alignment by using a sensor having a large aperture light-receiving lens or wide light-receiving plane is considered. However, such a solution could result in an undesirable result such as a larger ophthalmic measurement apparatus and higher cost/complicatedness of the system.

Therefore, as an alignment device of an ophthalmic measurement apparatus for solving the problem, a system is also known where the above-described bright spot image is formed on the imaging device of the imaging optical system as a central bright spot image, four index lights are projected onto the pupil rim of the cornea of the eye to be examined, four bright spot images from the pupil rim are formed on the imaging device as rim bright spot images, and when one of the rim bright spot images is formed on the imaging device, imaging optical system is driven to operate horizontally and vertically by a three-dimensional driving device to perform automatic alignment such that the remaining three bright spot images are formed on the imaging device based on the rim bright spot images, and a detection region in horizontal and vertical (XY) directions is expanded (for reference, see Japanese Patent No. 3606706).

However, even in the alignment method using four rim bright spot images, automatic alignment does not start until one of the rim bright spot images is formed on the imaging device, rim bright spot images come out of focus and do not become sharp when the working distance between the cornea of the eye to be examined and the imaging optical system is largely shifted, and automatic alignment does not start even if the rim bright spot images are formed on the imaging device.

SUMMARY OF THE INVENTION

Therefore, an object of the present invention is to provide an alignment device of an ophthalmic measurement apparatus, which is capable of using in a wide range and has a high accuracy.

To achieve the above object, an alignment device for an ophthalmic measurement apparatus according to one embodiment of the present invention includes an index projection optical system that forms a plurality of indices on cornea of an eye to be examined by projecting a plurality of index lights onto the cornea; an imaging optical system that forms the image of the plurality of indices on an imaging device as index images; a three-dimensional driving device for driving the imaging optical system in a three-dimensional direction; and a controlling device for controlling to drive the three-dimensional driving device.

In addition, the controlling device vertically and horizontally controls to drive the imaging optical system by the three-dimensional driving device such that a cornea vertex position of the image of the eye to be examined, which is formed on the imaging device, moves toward the center of the imaging device based on a position of the index image formed on the imaging device.

Moreover, the imaging optical system is configured to detect reflected light of the plurality of index lights reflected from the cornea by the imaging device, and the controlling device controls to drive the three-dimensional driving device such that average light quantity values become approximately equal in a plurality of photo-detecting sections of the imaging device where the reflected light is detected.

DETAILED DESCRIPTION OF THE PREFERRED EMBODIMENTS

Hereinafter, preferred embodiments of this invention will be described in detail based on the drawings.

Figure 1A:
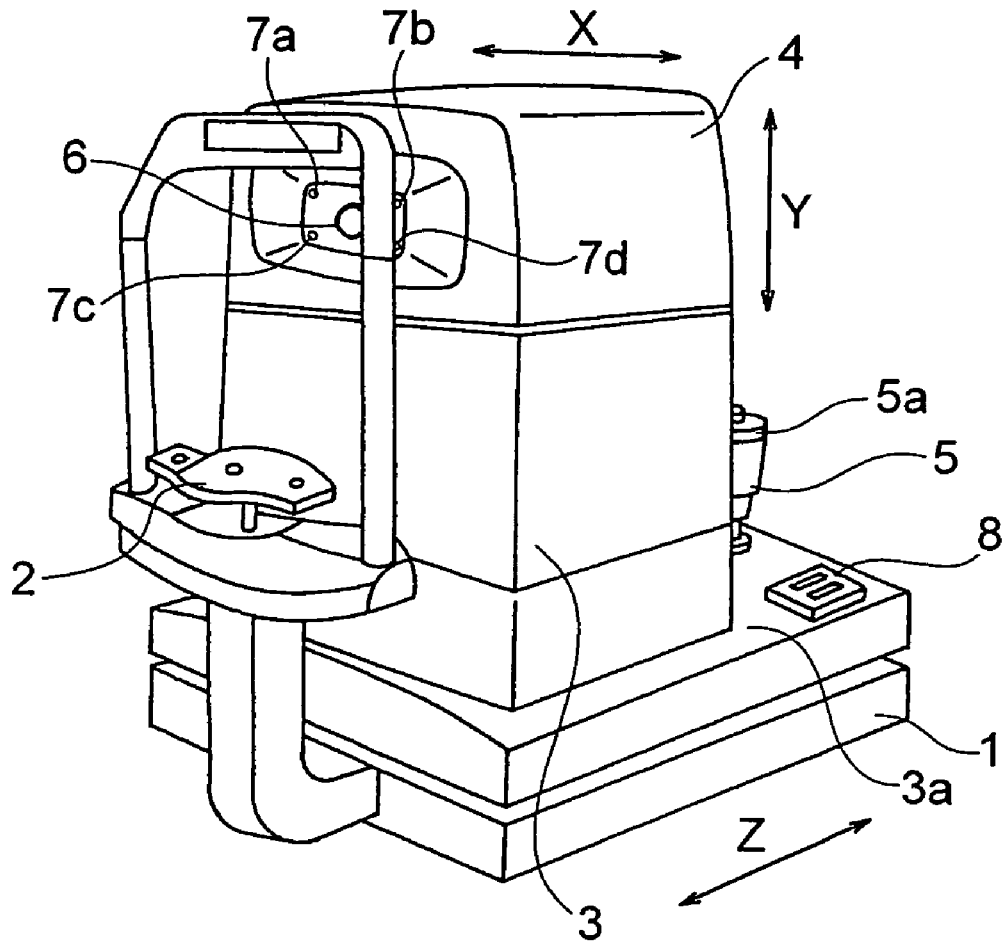
FIG. 1A is an external schematic view of a noncontact tonometer being an embodiment.

FIG. 1A shows the external schematic view of the noncontact tonometer being an embodiment. In FIG. 1A, reference numeral 1 denotes a base, and a chin receiver 2 for fixing the eye to be examined is provided for the base 1 in a fixed manner. Reference numeral 3 denotes a main body portion, and 4 an ophthalmic unit (measuring section) that houses an optical system (described later), and 5 an operation lever for moving the main body portion 3 and the ophthalmic unit 4.

By operating the operation lever 5, the main body portion 3 moves on the horizontal plane of the base 1 in back and forth directions (Z-direction) and horizontal directions (X-direction) in a sliding manner, and the ophthalmic unit 4 moves in vertical directions (Y-direction) to the main body portion 3.

Note that a spherical area (not shown) is provided on a middle portion in the vertical directions of the shaft of the operation lever 5, and the spherical area is rotatably held by a sphere-receiving portion (not shown) inside the main body portion 3. Thus, the operation lever 5 can be operated in a tilted movement in any direction around the spherical area (not shown). Further, a sliding plate (not shown) is held at the lower end portion of the shaft of the operation lever 5, and a friction plate (not shown) contacting the sliding plate (not shown) is adhered on the top surface of the base 1.

With this constitution, when the operation lever 5 is operated in a tilted movement, the main body portion 3 is operated to move to the base 1. Because a widely known constitution can be adopted for the constitution, its detailed illustration is omitted.

Further, a rotating knob 5a is held freely rotatably around an axis line on the upper portion of the operation lever 5, and a rotation amount detecting sensor (not shown) is installed between the lower end portion of the rotating knob 5a and the shaft of the operation lever 5. The rotation amount detecting sensor has a slit plate (not shown) held by the lower end portion of the rotating knob 5a, and a light source and a light-receiving device disposed at positions sandwiching the slit plate. The light source and the light-receiving device are attached to areas (not shown) of the shaft of the operation lever 5. Then, the rotation amount detecting sensor, when the rotating knob 5a is operated to rotate around the axis line, detects a rotating direction and a rotation amount of the rotating knob 5a from the signal of the light-receiving device. In addition, based on a detection result of the rotating direction and the rotation amount of the rotating knob 5a, a Y-axis motor (not shown in FIG. 1) that vertically moves the ophthalmic unit 4 is controlled to drive.

Since the constitution described in Japanese Patent Laid-Open No. 6-7292 (operation lever mechanism of an ophthalmic measurement apparatus) can be adopted for the details of the operation lever 5, the rotating knob 5a or the like, its detailed explanation will be omitted.

Further, the ophthalmic unit 4 also moves in horizontal directions (X-direction) and back and forth directions (Z-direction) to the main body portion 3. Such movement is not done by the operation lever 5 but by an X-axis motor (not shown in FIG. 1) and a Z-axis motor (not shown in FIG. 1) which are controlled and driven by the control circuit (described later).

These X-axis motor, Y-axis motor and Z-axis motor constitute three-dimensional driving device (three-dimensional driving device) for driving the ophthalmic unit 4 in a three-dimensional direction.

Figure 1B:
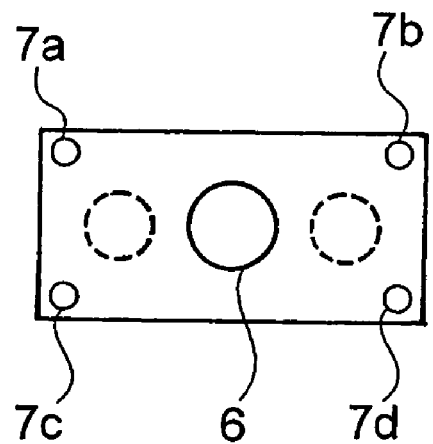
FIG. 1B is an explanatory view of a light source for illuminating the front eye portion of FIG. 1A.

Reference numeral 6 denotes a nozzle portion where nozzles for ejecting compressed air toward the eye to be examined are arranged. On a side of an ophthalmic unit 4 closer to a person to be examined, four light sources 7a to 7d, which project the alignment index around the cornea of the eye to be examined by using the nozzle portion 6 as a center, are arranged as shown in FIG. 1A and FIG. 1B. Note that the four light sources 7a to 7d are arranged close to the nozzle portion 6, so that it is easy to project the alignment index on the front eye portion of the eye to be examined. Further, on a side portion of the main body portion 3, a knob 8 for controlling movement limit where the nozzle portion 6 can approach the eye to be examined is arranged. Further, on the operation lever 5 side (examiner side) of the main body portion 3, a TV monitor for observation is provided.

<Alignment Optical System>

Figure 2:
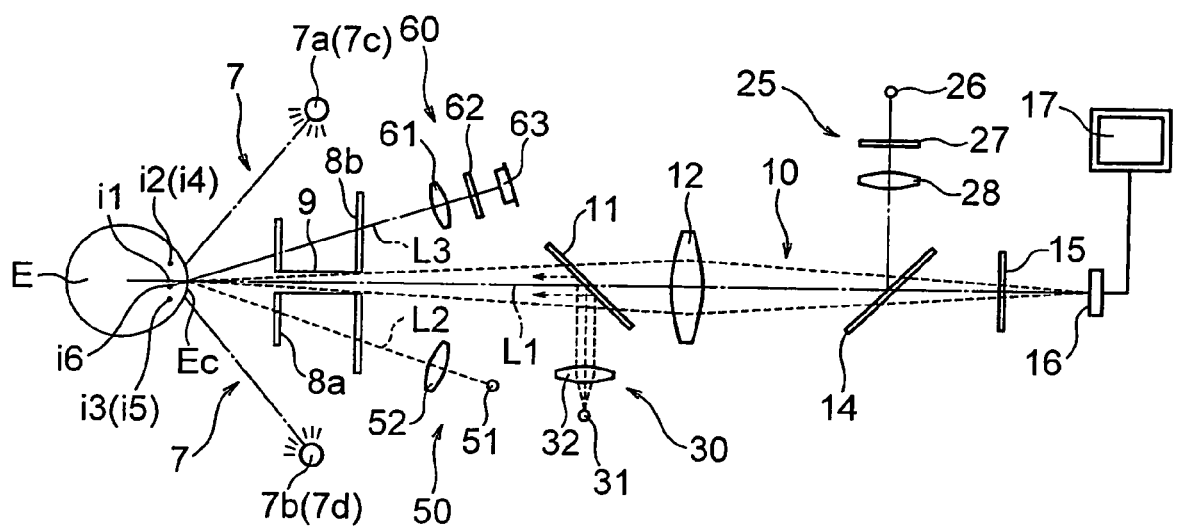
FIG. 2 is a principal portion constitution view of an alignment optical system of the noncontact tonometer being an embodiment.

FIG. 2 is the principal portion constitution view of the alignment optical system of the apparatus, which is a view seen from above. Note that the noncontact tonometer blows compressed air to the cornea of the eye to be examined to deform it into a predetermined shape, and measures intraocular pressure of the eye to be examined based on the air pressure directly or indirectly detected at that time, but explanation of the measurement mechanism itself will be omitted because it is not closely related to the present invention. For details, refer to Japanese Patent Laid-Open No. 4-297226 (title of the invention: Noncontact tonometer) of this applicant.

(Observation Light System)

Figure 4:
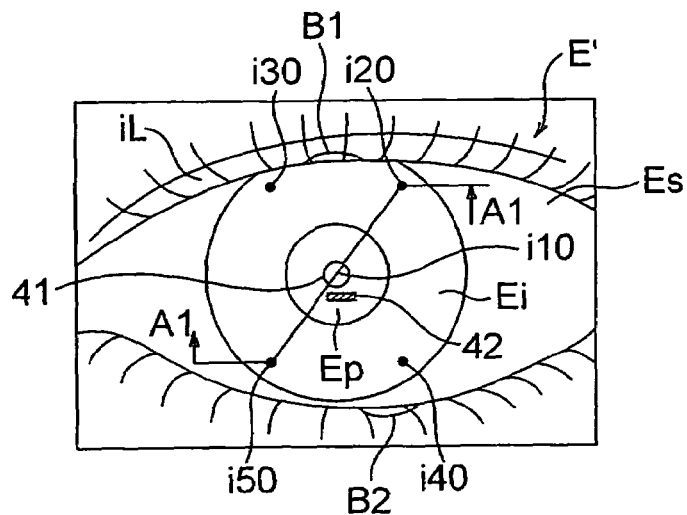
FIG. 4 is a view showing a screen example displayed on a TV monitor when the eye to be examined is aligned into a proper state.

Reference numeral 10 denotes an observation light system (imaging optical system), and L1 denotes its optical axis. The observation optical system 10 combines an index detection optical system that detects an index (described later) for the first and the second alignment in horizontal and vertical directions. On the optical path of the observation optical system 10, a nozzle 9 that ejects air for deforming the cornea is arranged while being held by glass plates 8a, 8b, and its axis matches the optical axis L1. On the optical axis L1, a beam splitter 11, an objective lens 12, a beam splitter 14, a filter 15, and a CCD camera 16 as an imaging device (area CCD in the drawing) are arranged. The filter 15 transmits the first and the second alignment index optical system (described later), has a non-transmitting characteristic to visible light and optical flux (wavelength 800 nm) of a distance index projection optical system (described later), and it prevents unnecessary noise light from entering the CCD camera 16, Then, when the image of the front eye portion of the eye to be examined E in FIG. 2 is captured by the CCD camera 16, the front eye portion image E' of the eye to be examined E is displayed on a TV monitor (display device) 17 by the image signal (video signal) from the CCD camera 16 as shown in FIG. 4. At this point, the front eye portion image E' is displayed on the TV monitor (display device) 17 together with an index image (described later), and the examiner observes this. Note that the front eye portion image E' has a pupil portion Ep, an iris portion Ei, a sclera portion Es and the like in FIG. 4. Further, a CRT, a liquid crystal indicator, or a monitor of a plasma method can be used as the display device (display device).

(Fixation Optical System)

A fixation optical system 25 has a light source 26 emitting visible light, a fixation target plate 27, and a projection lens 28. An optical flux outputted from the fixation target plate 27 by turning on the light source 26 passes the nozzle 9 through a projection lens 28, the beam splitter 14, the objective lens 12, and the beam splitter 11, and enters the eye to be examined.

(The First Alignment Index Projection Optical System)

Reference numeral 30 denotes the first alignment index projection optical system (the first index light projecting device). Reference numeral 31 denotes a central index projection light source, and 32 denotes a projection lens. The light source 31 outputs infrared light having the wavelength of 950 nm. An infrared optical flux outputted from the light source 31 is transformed into a parallel optical flux by the projection lens 32, and then, reflected by the beam splitter 11, passes through the nozzle 9 along the optical axis L1 to be irradiated on the cornea Ec of the eye to be examined E as the first index light, and reflected on the cornea Ec. Then, an optical flux having specular reflection on the cornea Ec forms the first alignment index (the first index) i1 being the virtual image of light source 31 on the eye to be examined E as a central index. The optical flux of the first alignment index i1 forms an index image (the first index image) i10 (the first bright spot image) of the first alignment index i1 on the CCD camera 16 being the imaging device.

Note that the first index light, by forming its image on the ½ area of radius of curvature on the cornea Ec of the eye to be examined E, forms the first index image (the first bright spot image) i10 of the first alignment index i1 being the first bright spot image on the CCD camera 16 being the imaging device. The first index image i10 formed on the CCD camera 16 is displayed on the screen of the TV monitor 17 in FIG. 2 together with the front eye portion image E' of the eye to be examined as shown in FIG. 4. At this point, the first index image i10 is displayed so as to be positioned at the center of the pupil portion Ep of the front eye portion image E'.

(The Second Alignment Index Projection Optical System)

The second alignment index projection optical system 7 (the second index light projecting device) has four light sources 7a to 7d (refer to FIG. 1). The light sources 7a, 7b and the light sources 7c, 7d are arranged at the same height and distance sandwiching the optical axis L1 to make the optical distance of the index equal. The light sources 7a to 7d output infrared light having the wavelength of 950 nm that is the same as that of the light source of the first alignment index projection optical system.

Lights from the light sources 7a, 7b are irradiated from an obliquely upper direction toward an area around the pupil of the cornea Ec of the eye to be examined, and form indices (the second indices) i2, i3 being the virtual images of the light sources 7a, 7b near the rim of pupil of the eye to be examined as rim indices (the second bright spot). Further, the light sources 7a, 7b combine light sources for detecting the open level of a lid (described later).

Lights from the light sources 7c, 7d are irradiated from an obliquely lower direction toward an area around the cornea of the eye to be examined, and form indices (the second indices) i4, i5 being the virtual images of the light sources 7c, 7d near the rim of pupil of the eye to be examined as rim indices (the second bright spot). The light sources 7a to 7d combine light sources for illumination, which illuminate the front eye portion of the eye to be examined.

The optical flux of the four indices i2, i3, i4, i5 enters the CCD camera 16 via the observation optical system 10, and forms index images i20, i30, i40, i50 (the second index images) on the imaging device of the CCD camera 16 as the imaging device. Then, these index images i20, i30, i40, i50 (the second index images) are displayed on the screen of the TV monitor 17 in FIG. 2 together with the front eye portion image E' of the eye to be examined as shown FIG. 4. At this point, index images i20, i30, i40, i50 (the second index images) are displayed so as to be positioned on the rim of the iris portion Ei of front eye portion image E'.

(Distance Index Projection Optical System)

Reference numeral 50 denotes a distance index projection optical system, and L2 denotes its optical axis. The optical axis L2 is provided in a tilted manner to the optical axis L1, and both optical axes intersect at a position apart from the nozzle 9 by a predetermined working distance. Reference numeral 51 denotes a light source for projecting distance index, which outputs light having the wavelength of 800 nm different from that of the light sources 7a to 7d and the light source 31, and 52 denotes a projection lens.

Light outputted from the light source 51 is transformed into parallel optical flux by the projection lens 52, and is irradiated onto the cornea Ec along the optical axis L2. The optical flux that made specular reflection on the cornea Ec forms an index i6 being the virtual image of the light source 51.

(Distance Index Detection Optical System)

Reference numeral 60 denotes a distance index detection optical system, and L3 denotes its optical axis. Optical axis L3 and optical axis L2 are axes symmetrical to the optical axis L1, and the both optical axes of the optical axis L3 and the optical axis L2 intersect on the optical axis L1. On the optical axis L3, a light-receiving lens 61, a filter 62, and a one-dimensional detecting device 63 are arranged. The filter 62 transmits the optical flux having the wavelength of 800 nm, which is outputted from the light source 51, has a non-transmitting characteristic to the optical flux of 950 nm outputted from the light sources 7a to 7d and the light source 31, and prevents noise light from entering the one-dimensional detecting device 63.

The cornea-reflected optical flux of the light source 51, which forms the index i6, enters the one-dimensional detecting device 63 via the light-receiving lens 61 and the filter 62. When the eye to be examined moves to the axis direction (back and forth directions) of the observation optical axis L1, the image of the index i6 also moves to the detecting direction of the one-dimensional detecting device 63, so that the position of the eye to be examined is detected from the deviation of the image of the index i6 on the one-dimensional detecting device 63.

<Controlling Device>

Figure 3:
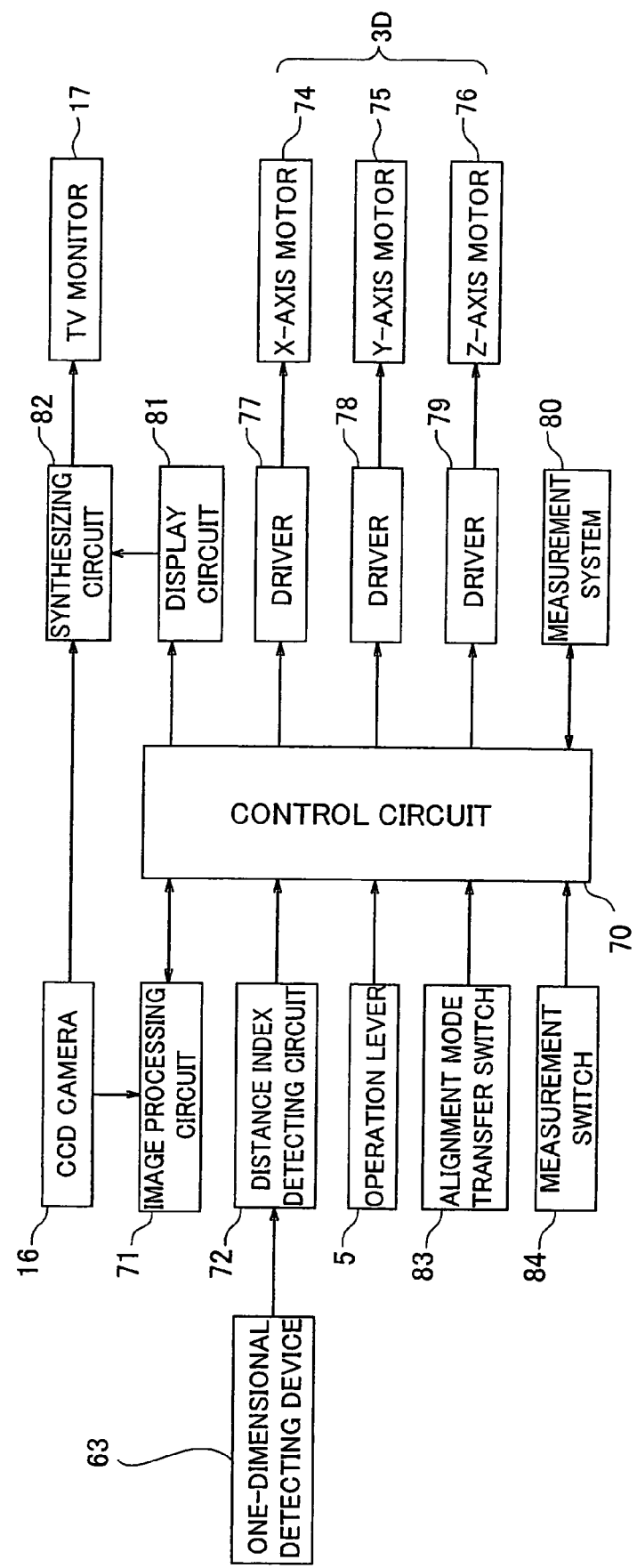
FIG. 3 is a principal portion constitution view of a control system of the noncontact tonometer being an embodiment.

FIG. 3 shows the principal portion constitution view of the controlling device of the apparatus. Reference numeral 70 denotes a control circuit, 71 denotes an image processing circuit, and 72 denotes a detection processing circuit of distance index. Reference numerals 74 to 76 denote X-axis, Y-axis and Z-axis motors that drive the ophthalmic unit 4 to the main body portion 3, and 77 to 79 denote drive circuits of each motor. The X-axis motor 74, Y-axis motor 75 and Z-axis motor 76 constitute the three-dimensional driving device 3D.

Reference numeral 80 denotes a measurement system, 81 a display circuit that generates character information, figures or the like, and 82 a synthesizing circuit. Reference numeral 83 denotes an alignment mode transfer switch, and it selects whether the alignment is set to automatic alignment performed by the apparatus based on index detection or is performed only by the examiner's operation using the operation lever 5. Reference numeral 84 denotes a measurement switch for inputting the signal of the start of measurement.

The image processing circuit 71 conducts image processing to a photographed image from the CCD camera 16, and inputs its processing result to the control circuit 70. The control circuit 70 obtains the positional information of the index image and pupil positional information by its input signals.

Further, the control circuit 70 obtains the deviation information of back and forth directions to the eye to be examined E by the signals from the one-dimensional detecting device 63, which are inputted via the detection processing circuit 72. The deviation information that the control circuit 70 obtained is sent to the display circuit 81, and the display circuit 81 generates a figure signal of distance mark and a positional signal on the TV monitor 17 based on the information. Output signals from the display circuit 81 are synthesized with video signals from the CCD camera 16 by the synthesizing circuit 82, and outputted on the TV monitor 17.

FIG. 4 is the view showing a screen example of the image E' of the eye to be examined, which is displayed on the TV monitor 17 when the XY directions are aligned in the proper state. In the state where the XY directions are aligned in a proper state, four index images (the second index image) i20, i30, i40, i50 formed around the cornea by the second alignment index projection optical system, and an index image (the first index image) i10 formed near the center of the cornea by the first alignment index projection optical system, are displayed. Reference numeral 41 denotes an alignment index (alignment mark) electrically generated by the pattern generator, and 42 denotes a distance mark. The distance mark 42 moves in real time corresponding to the distance between the cornea of the eye to be examined and the nozzle portion 6, and overlaps with the alignment index 41 when the cornea is in a proper working distance.

Further, the control circuit 70 divides the image, which is detected by the CCD camera 16 as the imaging device, into a plurality of light quantity detection areas in order to control the movement of the ophthalmic unit 4 in XY directions, calculates the average light quantity value of each light quantity detection area, and executes wide area alignment and precise alignment.

The control circuit 70 compares the calculated average light quantity values, and if an average light quantity value is higher than the average light quantity value of the other areas, there is an eye to be detected in the area or on the extended line of the area, so that the X-axis motor 74 and the Y-axis motor 75 are driven such that the visual axis (that is, the center of bright spot i1) of the eye to be examined E is directed to the standard position (optical axis of the observation light system) of the ophthalmic unit 4, and the ophthalmic unit 4 is moved horizontally and vertically. At this point, the ophthalmic unit 4 is moved such that the index image (cornea vertex) i10 is formed on the center of the CCD camera 16, and index image i10 comes in the alignment index 41, which is electrically generated by the pattern generator, on the screen of the TV monitor 17.

Then, when the average light quantity values become approximately equal, all index images can be detected and the index image i10 can be identified. In this case, the control circuit 70 calculates a position of center of gravity of each bright spot, drives the X-axis motor 74 and the Y-axis motor 75 based on the position to move the ophthalmic unit 4 horizontally and vertically until the index image i10 comes into the alignment index 41 that was electrically generated by the pattern generator.

[Operation]

Next, a description will be made for the action of the noncontact tonometer including the above-described constitution. Herein, an alignment action when the automatic alignment is selected will be mainly described.

An examiner fixes the eye to be examined by using the chin receiver 2, and the eye to be examined is allowed to focus on to a fixation target from the fixation optical system 25. When measurement becomes ready in this manner, the examiner operates the operation lever 5 or the like while observing the TV monitor 17, and rough aligns the ophthalmic unit 4 to the eye to be examined. The rough alignment is performed such that an area of the front eye portion of the eye to be examined E, which becomes lighter on the screen, can be observed. Specifically, rough alignment is performed such that the cornea Ec of the eye to be examined E comes into the CCD camera 16, and the cornea Ec is displayed on the TV monitor 17.

When the lighter area can be observed on the screen, the operation of the operation lever 5 is stopped (if necessary, a message instructing stopping may be displayed, or device for restricting the movement of the operation lever may be applied).

At this point, the control circuit 70 executes the following wide area alignment (when an index image is not on the monitor screen) and precise alignment.

(1) Wide Area Alignment (when an Index Image is not on the Monitor Screen)

The control circuit 70 divides an image detected by the CCD camera 16 as the imaging device into a plurality of light quantity detection areas, and calculates the average light quantity value of each light quantity detection area.

Figure 5:
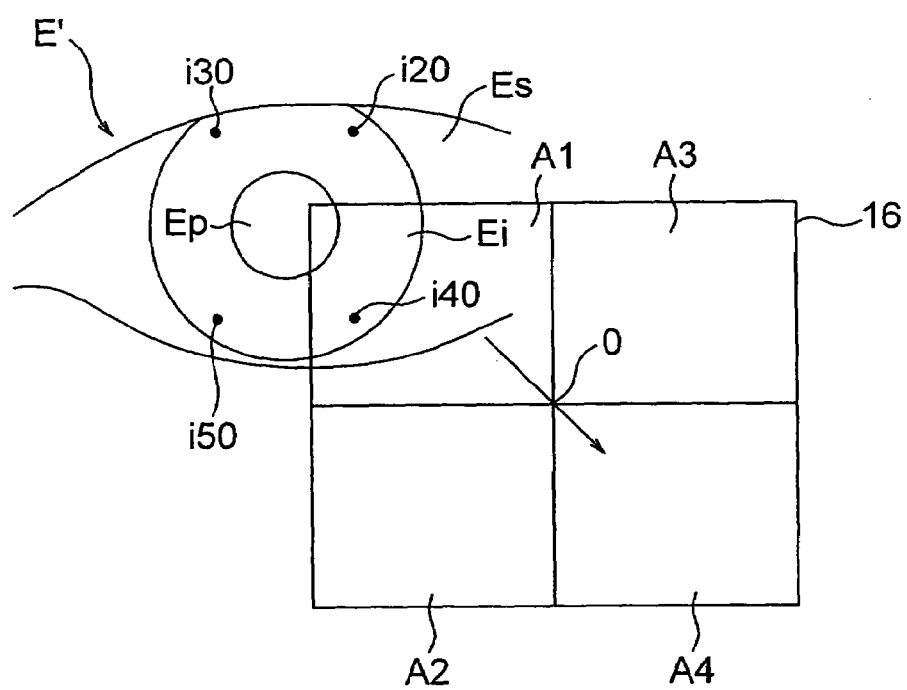
FIG. 5 is an explanatory view showing an example of a detection area for detecting light quantity value in a CCD camera of FIG. 2.
Figure 6:
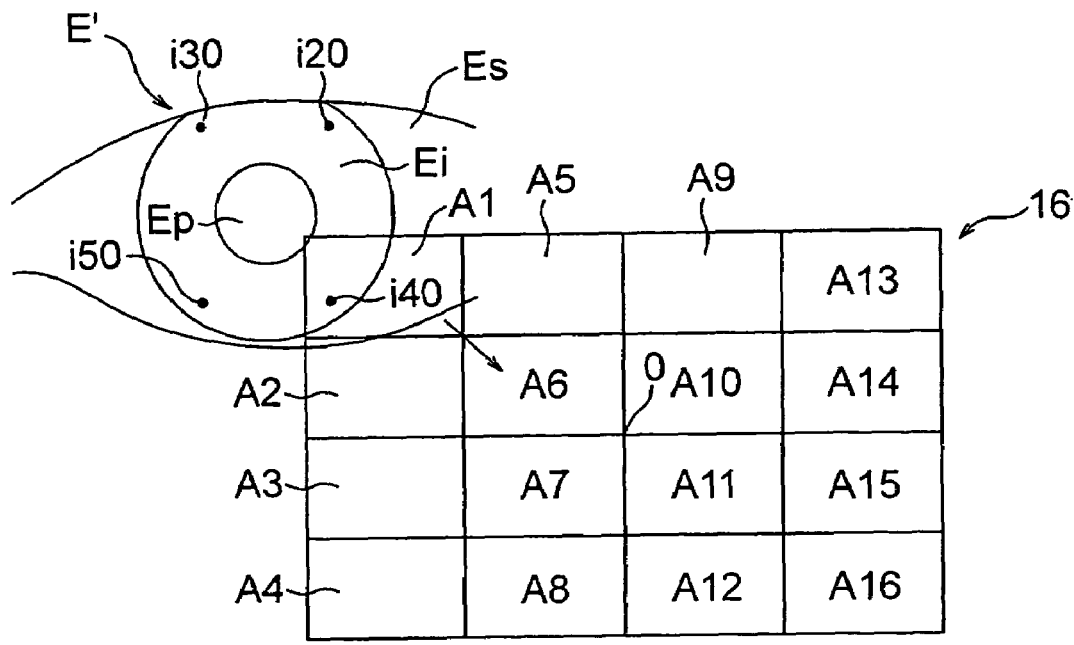
FIG. 6 is an explanatory view showing another example of the detection area for detecting light quantity value in the CCD camera of FIG. 2.

For example, as shown in FIG. 5, the circuit divides an image-receiving plane (light-receiving plane) of the CCD camera 16 as the imaging device into four (plural) detection areas (image-forming areas) A1 to A4, or as shown in FIG. 6, divides the image-receiving plane of the CCD camera 16 into 16 detection areas (image-forming areas) A1 to A16. Then, in the case of FIG. 5, average light quantity values $L_{av}1$ to $L_{av}4$ of each detection areas A1 to A4 are calculated. Further, in the case of FIG. 6, average light quantity values $L_{av}1$, $L_{av}4$, $L_{av}13$, $L_{av}16$ of the detection areas A1, A4, A13, A16 at four corners out of the detection areas A1 to A16 are calculated.

Then, these calculated average light quantity values of the light quantity detection areas (between the average light quantity values $L_{av}1$ to $L_{av}4$ in FIG. 5, between the average light quantity values $L_{av}1$, $L_{av}4$, $L_{av}13$, $L_{av}16$ in FIG. 6) are compared, and when an average light quantity value is higher than the average light quantity value of the other light quantity detection areas, there is an eye to be detected in the light quantity detection area or on the extended line of the light quantity detection area, the X-axis motor 74 and the Y-axis motor 75 of the three-dimensional driving device 3D are controlled to drive by the control circuit 70 so as to be directed to a standard position (optical axis of the observation light system), and the ophthalmic unit 4 is moved horizontally and vertically.

For example, in the case of FIG. 5, when the average light quantity value $L_{av}1$ of the detection area A1 is higher than the average light quantity values $L_{av}1$ to $L_{av}4$ of the other detection areas (A2 to A4), the eye to be examined is on the detection area A1 side, so that the X-axis motor 74 and the Y-axis motor 75 are controlled to drive by the control circuit 70 such that the eye to be examined is moved to the detection area A4 side, and the ophthalmic unit 4 is moved horizontally and vertically (XY directions).

Figure 7:
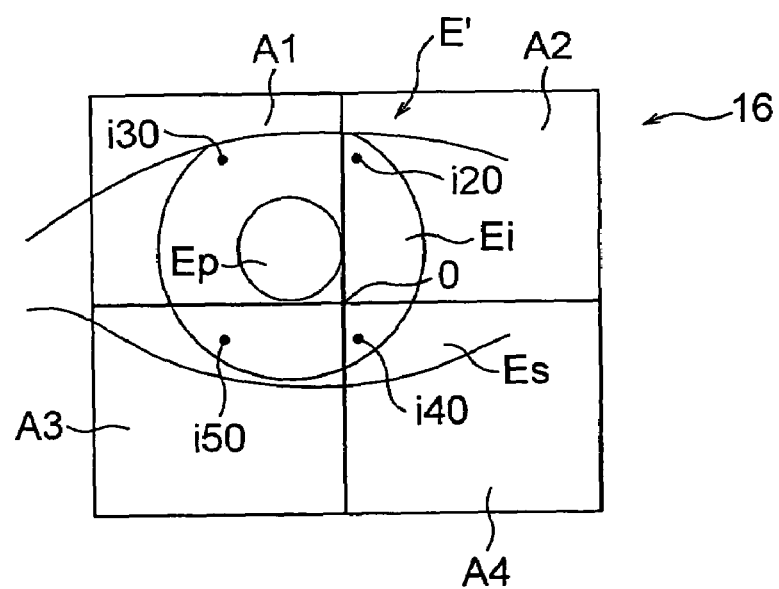
FIG. 7 is an explanatory view for explaining an action of the detection area of FIG. 5.

With this movement, when index images (the second index images) i20, i30, i40, i50 can be detected in all detection areas A1 to A4 from the state of FIG. 5 to the one shown in FIG. 7, the average light quantity values $L_{av}1$ to $L_{av}4$ of the detection areas A1 to A4 become approximately equal.

Further, in the case of FIG. 6, when the average light quantity value $L_{av}1$ of the detection area A1 is higher than the average light quantity value $L_{av}4$, $L_{av}13$, $L_{av}16$) of the other detection areas A4, A13, A16, the eye to be examined is on the detection area A1 side, so that the X-axis motor 74 and the Y-axis motor 75 are controlled to drive by the control circuit 70 such that the eye to be examined is moved to the detection area A16 side, and the ophthalmic unit 4 is moved horizontally and vertically (XY directions).

Figure 8:
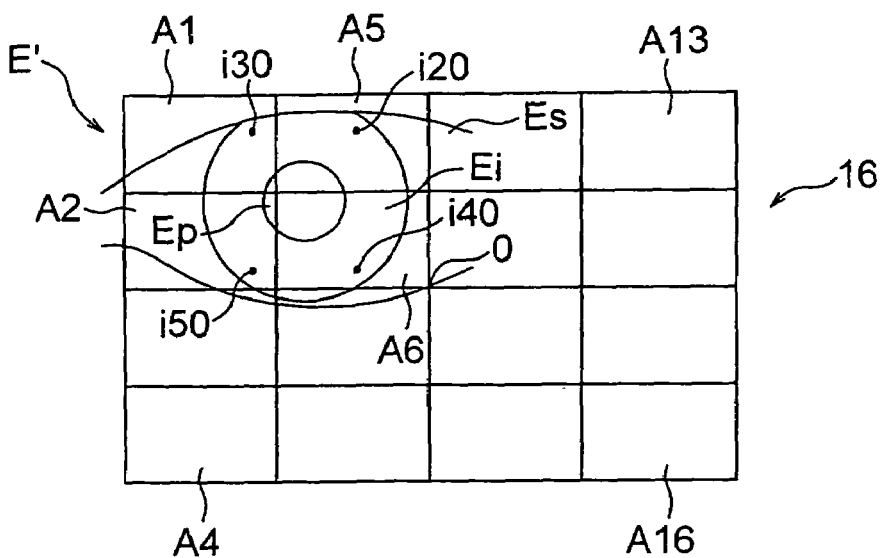
FIG. 8 is an explanatory view for explaining an action of the detection area of FIG. 6.

With this movement, when index images (the second index images) i20, i30, i40, i50 can be detected in all of the detection area A1 and its adjacent detection areas A2, A5, A6 from the state of FIG. 6 to the one shown in FIG. 8, the average light quantity values $L_{av}1$, $L_{av}2$, $L_{av}5$, $L_{av}6$ of the detection areas A1, A2, A5, A6 become approximately equal.

However, in this case, an object is to make average light quantity value of each light quantity detection area is made approximately equal to each other, so that when the average light quantity values become approximately equal, alignment is performed based on the following conditions.

(2) Precise Alignment

When the average light quantity value of each light quantity detection area become approximately equal to each other, all index images (the second index images) i20, i30, i40, i50 can be detected and the index image i10 can be identified, so that the position of center of gravity of the index images i20, i30, i40, i50 being each bright spot is calculated as the central position of the index image i10, and until the image of the central position of the index image i10 is formed on the center O of the CCD camera 16 based on the calculated position of center of gravity, that is, until the pattern generator allows the index image i10 to come into the electrically generated alignment index, the X-axis motor 74 and the Y-axis motor 75 are driven to move the ophthalmic unit 4 horizontally and vertically.

Note that the apparatus is capable of accelerating total alignment by making the moving speed of the ophthalmic unit 4 in X and Y directions be different in the wide area alignment and the precise alignment.

Then, when the index image i10 comes into the second allowable region, (when it comes into the electrically generated alignment index 41 by the pattern generator), the control circuit 70 stops driving in X and Y directions and determines the suitability of working distance. In the state where the optical flux of the index i1 by the distance index projection optical system enters the one-dimensional detecting device 63, the control circuit 70 obtains shift information in Z-direction based on the signal from the one-dimensional detecting device 63, drives the Z-axis motor 76 based on the shift information, and moves the ophthalmic unit 4 back and forth.

At this point, the distance mark 42 is displayed on the TV monitor 17. Then, the distance mark 42 moves in real time with the back and forth movement of the ophthalmic unit 4, and when the cornea Ec is in a proper working distance to the measuring section (an observation optical system being an imaging optical system) 4, the mark overlaps with the alignment index 41. (If the distance mark 42 is not displayed, the operation lever 5 becomes an operable state, and the examiner performs back and forth adjustment in a direction where the index image i10 in the alignment index 41 comes into focus.)

When Z-direction is set to a proper state, the control circuit 70 stops the back and forth movement of the ophthalmic unit 4, and this time, judges whether the index image i10 is within the first allowable region. When it is outside the region, fine adjustment movement is performed to the ophthalmic unit 4 in X and Y directions for a predetermined time to bring the image within the first allowable region. The moving speed at this point should be slower speed than the previous case of movement in X and Y directions (wide area alignment). Thus, the index image i10 is prevented from passing the first allowable region, and finely adjusted alignment in X and Y directions can be easily performed.

Further, index images to be projected toward an area around the cornea of the eye to be examined are four in the embodiment, but alignment state can be judged when at least two index images are projected. Index images to be projected may be larger than four.

Meanwhile, since the index image i10 is identified based on the positional relationship of the index images in the above-described guiding method of the ophthalmic unit 4, there is a possibility that another index image or disturbance light is identified as the index image i10 due to the influence of disturbance light. In this case, since the guidance of the ophthalmic unit 4 becomes unstable, even if an image is identified as the index image i10, the unit is not allowed to move if the index image is not within a predetermined region (within a region equivalent to the diameter of the nozzle 9) around the standard position on the CCD camera 16.

Further, an index image to be projected is blinked and by taking the difference between an image when it is turned ON and an image when it is not turned ON, the image of disturbance light can be removed. Accordingly, malfunction of automatic alignment can be prevented.

As described above, the alignment device of the ophthalmic measurement apparatus of the embodiment according to this invention is provided with: the index projection optical system that forms a plurality of indices (i2 to i5) on the cornea Ec of the eye to be examined E by projecting a plurality of index lights onto the cornea Ec; the imaging optical system (observation optical system 10) that forms the images of the plurality of indices (i2 to i5) as the index images (i20 to i50) on the imaging device (CCD camera 16); the three-dimensional driving device 3D that drives the imaging optical system (observation optical system 10) in a three-dimensional direction; and the controlling device (control circuit 70) that controls to drive the three-dimensional driving device 3D. In addition, the controlling device (control circuit 70), based on the positions of the index images (i20 to i50) whose images are formed on the imaging device (CCD camera 16), vertically and horizontally controls to drive the imaging optical system (observation optical system 10) by the three-dimensional driving device 3D such that the cornea vertex position (a position corresponding to the index i1 being a bright spot) of the image of the eye to be examined, whose image is formed on the imaging device (CCD camera 16) moves toward the center of the imaging device (CCD camera 16).

In addition, the imaging optical system (observation optical system 10) allows the imaging device (CCD camera 16) to detect the reflected lights of the plurality of index lights reflected from the cornea Ec, and the controlling device (control circuit 70) controls to drive the three-dimensional driving device 3D such that average light quantity values (for example, $L_{av}1$ to $L_{av}4$, or $L_{av}1$, $L_{av}2$, $L_{av}5$, $L_{av}6$) become approximately equal in a plurality of photo-detecting sections (for example, A1 to A4 or A1, A2, A5, A6) of the imaging device (C CD camera 16), where the reflected light is detected.

Moreover, in the alignment device of the ophthalmic measurement apparatus of the embodiment according to this invention, the plurality of photo-detecting sections (for example, A1 to A4 or A1, A2, A5, A6) are arranged in a plurality of photo-detecting regions (A1 to A4, A1 to A16) that the controlling device formed by dividing an image captured by the imaging device (CCD camera 16), and the controlling device (control circuit 70) calculates the average light quantity values (for example, $L_{av}1$ to $L_{av}4$, or $L_{av}1$, $L_{av}2$, $L_{av}5$, $L_{av}6$, or $L_{av}1$, $L_{av}4$, $L_{av}13$, $L_{av}16$) of the reflected lights by each detecting region (for example, A1 to A4, or A1, A2, A5, A6, or A1, A4, A13, A16), compares the calculated average light quantity values (for example, $L_{av}1$ to $L_{av}4$, or $L_{av}1$, $L_{av}2$, $L_{av}5$, $L_{av}6$, or $L_{av}1$, $L_{av}4$, $L_{av}13$, $L_{av}16$) of each detecting region, and controls to drive the three-dimensional driving device in a direction where the average light quantity value in a detecting region having a low average light quantity value becomes higher.

According to the alignment device of the ophthalmic measurement apparatus, automatic alignment can be started even if the bright spot images (index images i20 to i50 being the bright spot images) are not formed on the imaging device (CCD camera 16), and automatic alignment can be performed even if the bright spot images (index images i20 to i50 being the bright spot images) are formed on the imaging device (CCD camera 16) out of focus, so that automatic alignment can be performed in a wide area and highly accurately.

In addition, the imaging device (CCD camera 16) is divided into a plurality of photo-detecting regions (A1 to A4, A1 to A16), average light quantity values (for example, $L_{av}1$ to $L_{av}4$, or $L_{av}1$, $L_{av}2$, $L_{av}5$, $L_{av}6$) by the reflected light from the cornea Ec are calculated by each detecting region (for example, A1 to A4 or A1, A2, A5, A6), and the calculated average light quantity values (for example, $L_{av}1$ to $L_{av}4$, or $L_{av}1$, $L_{av}2$, $L_{av}5$, $L_{av}6$) of each detecting region (for example, A1 to A4 or A1, A2, A5, A6) are compared with each other, so that it is difficult to be influenced from noise such as the disturbance light, and the driving direction of the ophthalmic unit can be surely calculated.

Further, the alignment device of the ophthalmic measurement apparatus of the embodiment according to this invention is provided with: an ophthalmic unit for which the imaging optical system (observation optical system 10) that guides the light from the eye to be examined E to the imaging device (CCD camera 16) is provided and which is movable in a three-dimensional direction; the three-dimensional driving device 3D that drives the ophthalmic unit in the three-dimensional direction; the first index light projecting device (the first alignment index projection optical system 30) that projects the first index light to the cornea of the eye to be examined along the optical axis of the imaging optical system (observation optical system 10) and forms the first index (i1) on the eye to be examined E; the second index light projecting device (the second alignment index projection optical system) that projects a plurality of the second index lights to the cornea Ec of the eye to be examined E from a direction different from the optical axis of the imaging optical system (observation optical system 10) and forms a plurality of the second indices (i2 to i5) on the eye to be examined E; and the controlling device (control circuit 70) that controls to drive the three-dimensional driving device 3D such that the first index image (i10) moves toward the center of the imaging device (CCD camera 16) based on the position of the first index image (i10) of the first index (i1) whose image is formed on the imaging device (CCD camera 16) via the imaging optical system (observation optical system 10).

In addition, the imaging optical system (observation optical system 10) allows the imaging device (CCD camera 16) to detect the reflected lights from the plurality of the second index light reflected by the cornea Ec, and the controlling device (control circuit 70) controls to drive the three-dimensional driving device 3D such that the average light quantity values (for example, $L_{av}1$ to $L_{av}4$, or $L_{av}1$, $L_{av}2$, $L_{av}5$, $L_{av}6$) become approximately equal in a plurality of photo-detecting sections (for example, A1 to A4 or A1, A2, A5, A6) of the imaging device (CCD camera 16) where the reflected lights are detected.

Furthermore, in the alignment device of the ophthalmic measurement apparatus of the embodiment according to this invention, the plurality of photo-detecting sections (for example, A1 to A4 or A1, A2, A5, A6) are arranged in a plurality of photo-detecting regions (A1 to A4, A1 to A16) that the controlling device formed by dividing an image captured by the imaging device (CCD camera 16), the controlling device (control circuit 70) calculates the average light quantity values (for example, $L_{av}1$ to $L_{av}4$, or, $L_{av}1$, $L_{av}2$, $L_{av}5$) $L_{av}6$, or $L_{av}1$, $L_{av}4$, $L_{av}13$, $L_{av}16$) of the reflected lights by each detecting region (for example, A1 to A4 or A1, A2, A5, A6 or A1, A4, A13, A16), compares the calculated average light quantity values (for example, $L_{av}1$ to $L_{av}4$, or $L_{av}1$, $L_{av}2$, $L_{av}5$, $L_{av}6$, or $L_{av}1$, $L_{av}4$, $L_{av}13$, $L_{av}16$) of each detecting region with each other, and controls to drive the three-dimensional driving device in a direction where the average light quantity value in a detecting region having a low average light quantity value becomes higher.

According to the alignment device of the ophthalmic measurement apparatus, automatic alignment can be started even if the bright spot images (index images i20 to i50 being the bright spot images) are not formed on the imaging device (CCD camera 16), and automatic alignment can be performed even if the bright spot images (index images i20 to i50 being the bright spot images) are formed on the imaging device (CCD camera 16) out of focus, so that automatic alignment can be performed in a wide area and highly accurately.

In addition, the imaging device (CCD camera 16) is divided into a plurality of photo-detecting regions (A1 to A4, A1 to A16), average light quantity values (for example, $L_{av}1$ to $L_{av}4$, or $L_{av}1$, $L_{av}2$, $L_{av}5$, $L_{av}6$) by the reflected light from the cornea Ec are calculated by each detecting region (for example, A1 to A4 or A1, A2, A5, A6), and the calculated average light quantity values (for example, $L_{av}1$ to $L_{av}4$, or $L_{av}1$, $L_{av}2$, $L_{av}5$, $L_{av}6$) of each detecting region (for example, A1 to A4 or A1, A2, A5, A6) are compared with each other, so that it is difficult to be influenced from noise such as the disturbance light, and the driving direction of the ophthalmic unit can be surely calculated.

Further, in the alignment method of an ophthalmic measurement apparatus of the embodiment according to this invention, a plurality of indices are formed on the cornea Ec of the eye to be examined E by projecting a plurality of index lights onto the cornea Ec, the images of the plurality of indices (i2 to i5) are formed on the imaging device (CCD camera 16) as the index images (i20 to i50) via the imaging optical system (observation optical system 10), and based on the positions of the index images (i20 to i50) formed on the imaging device (CCD camera 16), the three-dimensional driving device 3D controlled by the controlling device (control circuit 70) controls to drive the imaging optical system (observation optical system 10) vertically and horizontally such that the cornea vertex position (a position corresponding to the index i1 being bright spot) of the image of the eye to be examined, which is formed on the imaging device (CCD camera 16), moves toward the center of the imaging device (CCD camera 16).

In addition, reflected light of the plurality of index lights reflected by the cornea Ec is detected by the imaging device (CCD camera 16), and the controlling device (control circuit 70) controls to drive three-dimensional driving device 3D such that the average light quantity values (for example, $L_{av}1$ to $L_{av}4$, or $L_{av}1$, $L_{av}2$, $L_{av}5$, $L_{av}6$) become approximately equal in a plurality of photo-detecting sections (for example, A1 to A4 or A1, A2, A5, A6) of the imaging device (CCD camera 16) where the reflected light is detected.

Furthermore, in the alignment method of an ophthalmic measurement apparatus of the embodiment according to this invention, the plurality of photo-detecting sections (for example, A1 to A4 or A1, A2, A5, A6) are arranged in a plurality of photo-detecting regions (A1 to A4, A1 to A16) that the controlling device formed by dividing the image captured by the imaging device (CCD camera 16), the controlling device (control circuit 70) calculates the average light quantity values (for example, $L_{av}1$ to $L_{av}4$, or $L_{av}1$, $L_{av}2$, $L_{av}5$, $L_{av}6$, or $L_{av}1$, $L_{av}4$, $L_{av}13$, $L_{av}16$) of the reflected lights by each detecting region (for example, A1 to A4 or A1, A2, A5, A6 or A1, A4, A13, A16), compares the calculated average light quantity values (for example, $L_{av}1$ to $L_{av}4$, or, $L_{av}1$, $L_{av}2$, $L_{av}5$, $L_{av}6$, or $L_{av}1$, $L_{av}4$, $L_{av}13$, $L_{av}16$) of each detecting region with each other, and controls to drive the three-dimensional driving device in a direction where the average light quantity value of the detecting region having a low average light quantity value becomes higher.

According to the alignment method of an ophthalmic measurement apparatus, automatic alignment can be started even if the bright spot images (index images i10 to i50 being the bright spot images) are not formed on the imaging device (CCD camera 16), and automatic alignment can be performed even if the bright spot images (index image i10 to i50 being the bright spot images) are formed on the imaging device (CCD camera 16) out of focus, so that automatic alignment can be performed in a wide area and highly accurately.

In addition, the imaging device (CCD camera 16) is divided into a plurality of photo-detecting regions (A1 to A4, A1 to A16), average light quantity values (for example, $L_{av}1$ to $L_{av}4$, or $L_{av}1$, $L_{av}2$, $L_{av}5$, $L_{av}6$) by the reflected light from the cornea Ec are calculated by each detecting region (for example, A1 to A4 or A1, A2, A5, A6), and the calculated average light quantity values (for example, $L_{av}1$ to $L_{av}4$, or $L_{av}1$, $L_{av}2$, $L_{av}5$, $L_{av}6$) of each detecting region (for example, A1 to A4 or A1, A2, A5, A6) are compared with each other, so that it is difficult to be influenced from noise such as the disturbance light, and the driving direction of the ophthalmic unit can be surely calculated.

Meanwhile, in the case of calculating light quantity values by dividing the image captured by the imaging device (CCD camera 16) into a plurality of photo-detecting regions (A1 to A4, A1 to A16), the light quantity values may be calculated by dividing the imaging device (CCD camera 16) into a plurality of photo-detecting regions (A1 to A4, A1 to A16), or the light quantity values may be calculated by dividing a frame memory (not shown) as a plurality of photo-detecting regions when image signals captured by the imaging device (CCD camera 16) are built in the frame memory and displayed on the display device (TV monitor 17).

Further, although an example where the invention applied to a tonometer has been shown, the invention can be applied for the ophthalmic measurement apparatus of a fundus camera, a refractometer, a cornea endothelial cell photographing system or the like other than the tonometer.

In the above-described embodiment, the area of the CCD (a solid-state imaging device) is dividend into four when performing wide area alignment, but the invention is not necessarily limited to this. For example, it may be divided in two. The point is that the area should be divided into two or more.

Now, since time for taking values into a memory and processing time become shorter when the area to be divided and compared is limited in a small area, alignment time is made shorter than conventional detection of the center of gravity in bright spots by using the entire plane of a CCD.

Figure 9:
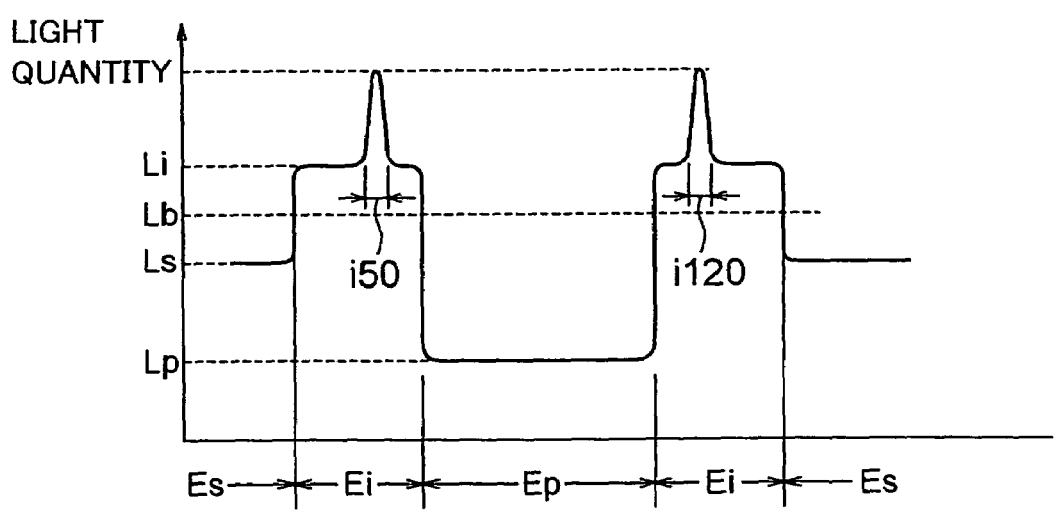
FIG. 9 is an explanatory view of light quantity distribution of an area taken along line A1-A1 of the front eye portion of FIG. 4.

Meanwhile, in the eye to be examined E of FIG. 2, light quantity values of reflected lights from positions corresponding to pupil, iris, sclera and the like (not shown) are different. In other words, on the front eye portion image E' of FIG. 4 that was captured by the reflected light from the eye to be examined E, light quantity values of the pupil portion Ep, the iris portion Ei and the sclera portion Es are different. FIG. 9 shows the light quantity distribution of the reflected light from the pupil, the position of the iris, sclera or the like of the eye to be examined E, that is, the distribution of light quantity values Lp, Li, Ls of the pupil portion Ep, the iris portion Ei, the sclera portion Es of FIG. 4. Further, since the index images i20, i50 overlap with the iris portion Ei, the light quantity values L20, L50 of the index images i20, i50 are larger than the light quantity value Li of the iris portion Ei.

In addition, in photographing the eye to be examined E by the CCD camera 16, a partially bright areas could occur on the rim of a lid (not shown) of the eye to be examined E or the lower rim of the eye to be examined E due to disturbance light. In other words, when the eye to be examined E of FIG. 2 is displayed on the TV monitor 17 as the front eye portion image E' as shown in FIG. 4, there are bright areas as shown in B1 and B2, for example, on the rim of lid image iL of the front eye portion image E' or the lower rim of the front eye portion image E'. The bright areas become noise in detecting the index images i20 to i50.

Because such influence by the reflection of disturbance light on the rim of lid or the like is expected, a slice level for calculating light quantity values is set, the position of the optical axis of the observation optical system of the ophthalmic unit 4 is determined from the average value of the light quantity values, which are calculated by using the slice level value as a boundary, and thus the influence of pupil, iris, sclera and disturbance light can be reduced. For example, a light quantity value Lb in the middle of the light quantity value Li of the iris portion Ei and the light quantity value Ls of the sclera portion Es is set as a light quantity value of the slice level, and light quantity value in each detection area may be calculated by using an area having higher light quantity value than the light quantity value Lb.

As described above, by dividing the CCD into a plurality of detection areas and calculating the average light quantity value of each detection area, and by comparing the calculated average light quantity values of a plurality of detection areas, detection range can be made wider and operation processing time can be shortened, so that alignment can be performed quickly and easily.

Further, areas having light quantity of the slice level or less (a dark region of pupil or the like) is complemented by using a value such as an average of the entire area, a predetermined value and a light quantity value of surrounding area, and light quantity value in each area may be calculated.

According to the above-mentioned alignment method for an ophthalmic measurement apparatus and the above-mentioned alignment device, automatic alignment can be started even if the bright spot images are not formed on the imaging device, and automatic alignment can be performed even if the bright spot images are formed on the imaging device out of focus, so that automatic alignment can be performed in a wide range and highly accurately.

Although the preferred embodiments of the present invention have been explained, it should be noted that the present invention is not limited to these embodiments, various modification and changes can be made to the embodiments.

What is claimed is:

1. An alignment device for an ophthalmic measurement apparatus, comprising:
   an index projection optical system that forms a plurality of indices on a cornea of an eye to be examined by projecting a plurality of index lights onto said cornea;
   an imaging optical system that forms the images of said plurality of indices on an imaging device as index images;
   a three-dimensional driving device for driving said imaging optical system in a three-dimensional direction; and
   a controlling device for controlling to drive said three-dimensional driving device,
   said controlling device, based on the positions of the index images formed on said imaging device, controlling to drive said imaging optical system vertically and horizontally by said three-dimensional driving device such that a cornea vertex position of the image of said eye to be examined, which is formed on said imaging device, moves toward the center of the imaging device, wherein
   said imaging optical system allows said imaging device to detect reflected lights of said plurality of index lights reflected by said cornea, and
   said controlling device controls to drive said three-dimensional driving device such that average light quantity values become approximately equal in a plurality of photo-detecting sections of said imaging device where said reflected lights are detected, wherein
   said plurality of photo-detecting sections are arranged in a plurality of photo-detecting regions that said controlling device formed by dividing an image captured by said imaging device, and
   said controlling device calculates the average light quantity values of said reflected lights by each of said detecting regions, compares the calculated average light quantity values of each detecting region with each other, and controls to drive said three-dimensional driving device in a direction where an average light quantity value in a detecting region having a low average light quantity value becomes higher.

2. The alignment device for an ophthalmic measurement apparatus according to claim 1, wherein the moving speed of said three-dimensional driving device is variable.

3. The alignment device for an ophthalmic measurement apparatus according to claim 1, wherein said imaging device is a CCD camera.

4. The alignment device for an ophthalmic measurement apparatus according to claim 1, further comprising a cornea vertex index projection optical system that projects cornea vertex index light onto a position where the radius of curvature of said cornea becomes half such that the cornea vertex index image is formed on said imaging device when the light is projected onto said cornea vertex position of said cornea.

5. The alignment device for an ophthalmic measurement apparatus according to claim 4, wherein said controlling device controls to drive said three-dimensional driving device such that said cornea vertex index image by said cornea vertex index light comes into an approximate center of said imaging device.

6. The alignment device for an ophthalmic measurement apparatus according to claim 1, further comprising:
   a distance index projection optical system that is obliquely provided to the optical axis of said imaging device optical system, and irradiates parallel optical flux on said cornea; and
   a distance index detection optical system having an optical axis that is provided symmetric to the optical axis of said distance index projection optical system with respect to the optical axis of said imaging optical system, and detecting the parallel optical flux of said distance index projection optical system, which is reflected on said cornea.

7. The alignment device for an ophthalmic measurement apparatus according to claim 6, wherein said control circuit controls to drive said three-dimensional driving device such that said plurality of index images are positioned on the rim of the iris portion of the front eye portion image of said eye to be examined.

8. The alignment device for an ophthalmic measurement apparatus according to claim 6, wherein
   said controlling device includes:
   an image processing circuit that conducts image processing to the photographed image of said imaging device and inputs an image signal obtained as a processing result to a control circuit;
   a control circuit that calculates the positional information of said index image and pupil positional information from said image signal; and
   a distance index detection processing circuit that inputs the deviation information in back and forth directions of said eye to be examined, which is obtained from the detecting device of said distance index detection optical system, to said control circuit.

9. The alignment device for an ophthalmic measurement apparatus according to claim 1, further comprising a fixation optical system that is provided along the optical axis of said imaging optical system and irradiates visible light onto said eye to be examined.

10. The alignment device for an ophthalmic measurement apparatus according to claim 1, wherein
    said index projection optical system projects a plurality of index lights onto the cornea of said eye to be examined by allowing the lights to blink, and
    said controlling device takes a difference between an image when the lights are turned ON and an image when the lights are not turned ON and identifies an index image.

11. The alignment device for an ophthalmic measurement apparatus according to claim 1, wherein average light quantity values of said divided plurality of detecting regions are calculated by dividing a frame memory into a plurality of detecting regions when image signals captured by said imaging device are built in the frame memory and displayed on a display device.

12. The alignment device for an ophthalmic measurement apparatus according to claim 1, wherein said ophthalmic measurement apparatus includes a tonometer, a fundus camera, a refractometer, and a cornea endothelial cell photographing device.

13. The alignment device for an ophthalmic measurement apparatus according to claim 1, wherein calculation of said average light quantity values is performed in a previously set range of a slice level.

14. An alignment device for an ophthalmic measurement apparatus, comprising:
an index projection optical system that forms a plurality of indices on a cornea of an eye to be examined by projecting a plurality of index lights onto said cornea;
an imaging optical system that forms the images of said plurality of indices on an imaging device as index images;
a three-dimensional driving device for driving said imaging optical system in a three-dimensional direction; and
a controlling device for controlling to drive said three-dimensional driving device,
said controlling device, based on the positions of the index images formed on said imaging device, controlling to drive said imaging optical system vertically and horizontally by said three-dimensional driving device such that a cornea vertex position of the image of said eye to be examined, which is formed on said imaging device, moves toward the center of the imaging device, wherein
said imaging optical system allows said imaging device to detect reflected lights of said plurality of index lights reflected by said cornea, and
said controlling device controls to drive said three-dimensional driving device such that average light quantity values become approximately equal in a plurality of photo-detecting sections of said imaging device where said reflected lights are detected, wherein
said plurality of photo-detecting sections are included in a plurality of photo-detecting regions that said controlling device formed by dividing an image captured by said imaging device at least into four, and
said controlling device calculates the average light quantity values of said reflected lights by each of said detecting regions, compares average light quantity values of detecting regions each including the four corners of said imaging device, and controls to drive said three-dimensional driving device in a direction where the average light quantity value of a detecting region having a low average light quantity value becomes higher.

15. The alignment device for an ophthalmic measurement apparatus according to claim 14, wherein said controlling device controls to drive said three-dimensional driving device such that average light quantity values become approximately equal in four regions adjacent to a detecting region having a high average light quantity value out of said detecting regions.

16. An alignment device for an ophthalmic measurement apparatus, comprising;
an ophthalmic unit that is provided with an imaging optical system that guides light from an eye to be examined to an imaging device and is movable in a three-dimensional direction;
a three-dimensional driving device for driving said ophthalmic unit in the three-dimensional direction;
a first index light projecting device for projecting the first index light onto the cornea of said eye to be examined along the optical axis of said imaging optical system and forming the first index on said eye to be examined;
a second index light projecting device for projecting a plurality of the second index lights onto the cornea of said eye to be examined from a direction different from the optical axis of said imaging optical system and forming a plurality of the second indices on said eye to be examined; and
a controlling device that controls to drive said three-dimensional driving device such that said first index image moves toward the center of said imaging device based on the position of the first index image of said first index, which is formed in said imaging device via said imaging optical system, wherein
said imaging optical system allows said imaging device to detect the reflected lights of said plurality of the second index lights reflected from said cornea, and
said controlling device controls to drive said three-dimensional driving device such that the average light quantity values become approximately equal in a plurality of photo-detecting sections of said imaging device where said reflected lights are detected, wherein
said plurality of photo-detecting sections are arranged in a plurality of photo-detecting regions that said controlling device formed by dividing an image captured by said imaging device, and
said controlling device calculates the average light quantity values of said reflected lights by each of said detecting regions, includes the calculated average light quantity values of each detecting region with each other, and controls to drive said three-dimensional driving device in a direction where an average light quantity value in a detecting region having a low average light quantity value becomes higher.

17. An alignment method for an ophthalmic measurement apparatus, comprising the steps of:
forming a plurality of indices on a cornea of an eye to be examined by projecting a plurality of index lights onto said cornea;
imaging said plurality of indices on an imaging device as index images via an imaging optical system;
controlling said imaging optical system to drive vertically and horizontally by a three-dimensional driving device which is controlled by a controlling device such that a cornea vertex position of the image of the eye to be examined, which is imaged on said imaging device, moves toward a center of said imaging device, based on positions of said index images imaged on said imaging device;
detecting reflected light of said plurality of index lights reflected from said cornea by said imaging device; and
controlling the drive of said three-dimensional driving device by said controlling device such that average light quantity values in a plurality of detecting sections of said imaging device where said reflected lights are detected become approximately equal, wherein
said plurality of photo-detecting sections are arranged in a plurality of photo-detecting regions that said controlling device formed by dividing an image captured by said imaging device, and
said controlling device calculates the average light quantity values of said reflected lights by each of said detecting regions, compares the calculated average light quantity values of each detecting region with each other, and controls to drive said three-dimensional driving device in a direction where an average light quantity value in a detecting region having a low average light quantity value becomes higher.

* * * * *